United States Patent
Hong et al.

(10) Patent No.: US 10,365,284 B2
(45) Date of Patent: Jul. 30, 2019

(54) KIT FOR DETECTING TARGET MATERIAL AND METHOD OF DETECTING TARGET MATERIAL USING THE SAME

(71) Applicant: ELECTRONICS AND TELECOMMUNICATIONS RESEARCH INSTITUTE, Daejeon (KR)

(72) Inventors: Hyo-Bong Hong, Daejeon (KR); Seung-Min Choi, Daejeon (KR); Jae-Chan Jeong, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/807,454

(22) Filed: Nov. 8, 2017

(65) Prior Publication Data

US 2018/0149655 A1  May 31, 2018

(30) Foreign Application Priority Data

Nov. 30, 2016  (KR) .......................... 10-2016-0161763

(51) Int. Cl.

| | |
|---|---|
| *G01N 33/574* | (2006.01) |
| *G01N 1/40* | (2006.01) |
| *G01N 33/543* | (2006.01) |
| *G01N 33/68* | (2006.01) |
| *B01L 3/00* | (2006.01) |

(52) U.S. Cl.
CPC ........ *G01N 33/57484* (2013.01); *B01L 3/505* (2013.01); *G01N 1/405* (2013.01); *G01N 1/4077* (2013.01); *G01N 33/543* (2013.01); *G01N 33/54346* (2013.01); *G01N 33/6893* (2013.01); *B01J 2219/00299* (2013.01); *G01N 33/54326* (2013.01); *G01N 2800/26* (2013.01)

(58) Field of Classification Search
CPC ............ G01N 33/57484; G01N 1/405; G01N 33/543; G01N 33/6893; G01N 33/54346; G01N 1/4077; G01N 33/54326; B01L 3/505

See application file for complete search history.

(56) References Cited

U.S. PATENT DOCUMENTS

| | | | |
|---|---|---|---|
| 6,037,186 A * | 3/2000 | Stimpson | B01J 19/0046 435/969 |
| 2001/0019827 A1* | 9/2001 | Dawson | B01J 19/0046 435/6.11 |
| 2001/0031495 A1* | 10/2001 | Tajima | B01L 3/505 435/287.2 |

(Continued)

FOREIGN PATENT DOCUMENTS

| | | |
|---|---|---|
| KR | 10-2012-0017884 A | 2/2012 |
| KR | 10-1243348 B1 | 3/2013 |

(Continued)

OTHER PUBLICATIONS

Krause et al., "Magnetic particle detection by frequency mixing for immunoassay applications", Journal of Magnetism and Magnetic Materials, Dec. 13, 2006, pp. 436-444, vol. 311, Elsevier B.V.

*Primary Examiner* — Melanie Brown

(57) ABSTRACT

This invention relates to a kit for detecting a target material and a method of detecting a target material using the same.

11 Claims, 6 Drawing Sheets

(56) References Cited

U.S. PATENT DOCUMENTS

| | | | |
|---|---|---|---|
| 2005/0181521 A1* | 8/2005 | Niskanen | G01N 33/558 436/514 |
| 2008/0193953 A1* | 8/2008 | Takizawa | G01N 33/54366 435/7.72 |
| 2008/0213906 A1* | 9/2008 | Aurand | B01J 20/06 436/63 |
| 2011/0237453 A1 | 9/2011 | Park et al. | |
| 2016/0223441 A1* | 8/2016 | Gjerde | C12N 1/02 |

FOREIGN PATENT DOCUMENTS

| | | |
|---|---|---|
| KR | 10-2013-0059304 A | 6/2013 |
| KR | 10-1515127 B1 | 4/2015 |
| KR | 10-2016-0025122 A | 3/2016 |
| KR | 10-1612094 B1 | 4/2016 |

\* cited by examiner

KIT FOR DETECTING TARGET MATERIAL AND METHOD OF DETECTING TARGET MATERIAL USING THE SAME

CROSS REFERENCE TO RELATED APPLICATION

This application claims the benefit of Korean Patent Application No. KR 10-2016-0161763, filed Nov. 30, 2016, which is hereby incorporated by reference in its entirety into this application.

BACKGROUND OF THE INVENTION

1. Technical Field

The present invention relates to a kit for detecting a target material and a method of detecting a target material using the same.

2. Description of the Related Art

The analysis of material able to act as a biomarker, such as DNA and protein, is regarded as very important in the fields of life science, medicine, chemistry, and chemical engineering. Although a variety of analysis methods have been developed for particular analytes, most biochemical analyses, other than molecular weight analysis (electrophoresis and MALDI-TOF mass spectrometry), are carried out in a manner in which DNA is analyzed through complementary bonding using cDNA (complementary DNA) or protein is analyzed using specific bonding of a specific protein such as an antibody and various kinds of compounds (mainly including organic materials) or using an enzyme-substrate reaction.

The most fundamental principle for such methods is that, regardless of the kind of analyte (DNA or protein), either a measurement object or a measurement material is immobilized on glass, a silicon wafer or plastic, after which physicochemical changes in a labeling compound are optically or electrochemically analyzed, thereby determining whether or not the material of interest is present.

Based on this principle, methods of measuring the extent of activation of the measurement object (or measurement material) using a fluorescent/luminescent/chromatic material or analysis methods using quantum dots (QDs) or magnetic beads are particularly useful.

However, such methods are problematic because analysis may be delayed due to the use of the enzyme reaction, or measurement results may vary when the amount of the enzyme to be treated is different. Furthermore, upon fluorescent measurement, a fluorescent analyzer is very expensive and the use thereof is not easy because it is greatly affected by external light, and fluorescent or chromatic measurement makes it impossible to analyze layers other than the uppermost layer when the measurement material is provided in the form of a layer structure.

SUMMARY OF THE INVENTION

Accordingly, the present invention is intended to provide a kit for detecting a target material, in which the treatment and analysis of a sample may be simultaneously performed using magnetic nanoparticles, and the area of a sample reaction unit may be adjusted.

In addition, the present invention is intended to provide a method of detecting a target material using the above kit.

Therefore, the present invention provides a kit for detecting a target material, comprising a hollow tube-shaped body, a sample injection port, a sample injection member, a first support, a first sample reaction unit, and a second support, wherein the front end of the body is provided with the sample injection port, the portion of the front end of the body other than the sample injection port is closed, the rear end of the body is formed with an opening into which the sample injection member is inserted, the body includes the first support, the first sample reaction unit and the second support, which are inserted therein, the first sample reaction unit is disposed between the first support and the second support, the first support is disposed so that the first sample reaction unit is not exposed to the front end of the body and the sample injection port, the second support is disposed so that the first sample reaction unit is not exposed to the opening of the body, the first sample reaction unit is a polymer thin film including magnetic nanoparticles on which an antibody specifically binding to the target material is immobilized, the polymer thin film is wound in a roll shape so as to form a hollow hole in a center thereof, and the central axis of the hollow hole is positioned perpendicular to a direction of injection of a sample.

In addition, the present invention provides a method of detecting a target material, comprising detecting whether or not the target material is present by injecting a sample into the kit of the present invention.

According to the present invention, a kit for detecting a target material can detect a sample in a close system and is thus effective at measuring infectious disease, etc.

Also according to the present invention, the area of the sample reaction unit of the kit for detecting a target material can be easily adjusted, and the kit can be conveniently used outdoors.

DESCRIPTION OF THE SPECIFIC EMBODIMENTS

Figure 1:
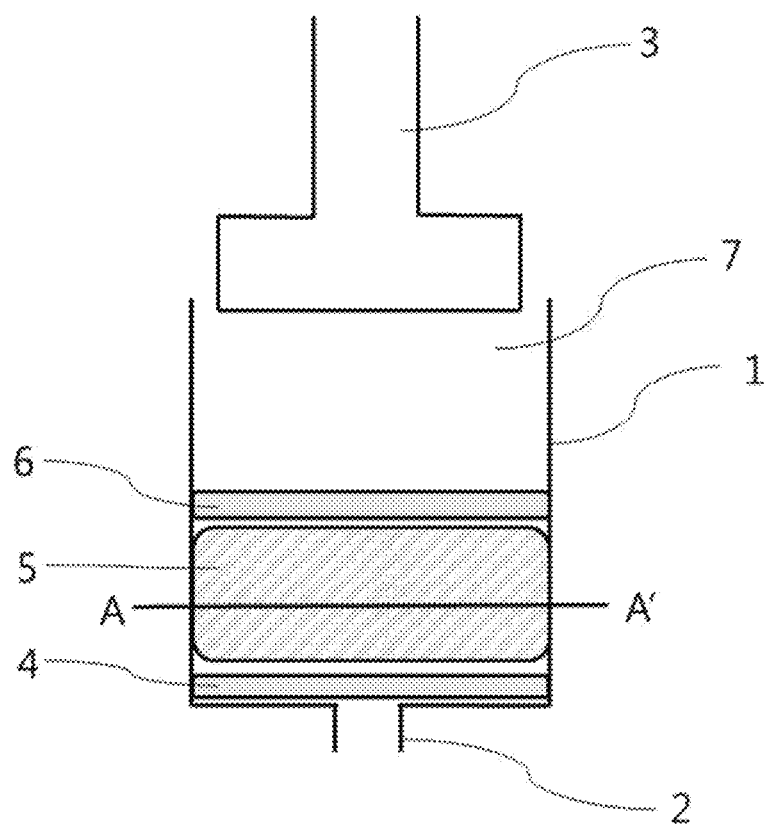
FIG. 1 is a side cross-sectional view showing a kit for detecting a target material according to the present invention, including a first support, a first sample reaction unit and a second support.
Figure 2:
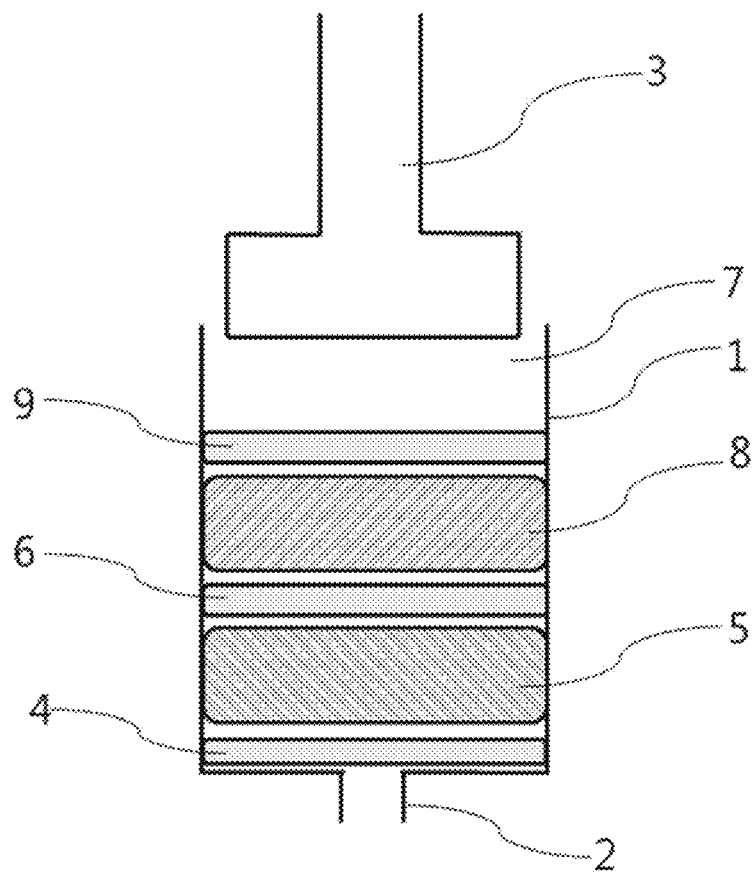
FIG. 2 is a side cross-sectional view showing a kit for detecting a target material according to the present invention, including a first support, a first sample reaction unit, a second support, a second sample reaction unit, and a third support.
Figure 3:
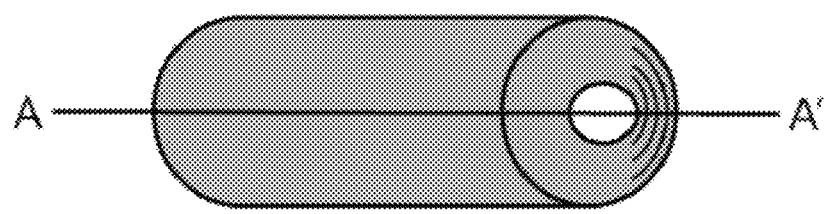
FIG. 3 shows the kit of FIG. 1, the sample reaction unit of which is wound in the direction of A and A'.
Figure 4:
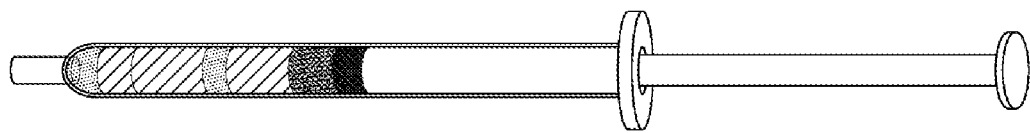
FIG. 4 is a photograph showing the kit for detecting a target material according to the present invention using a syringe.
Figure 5:
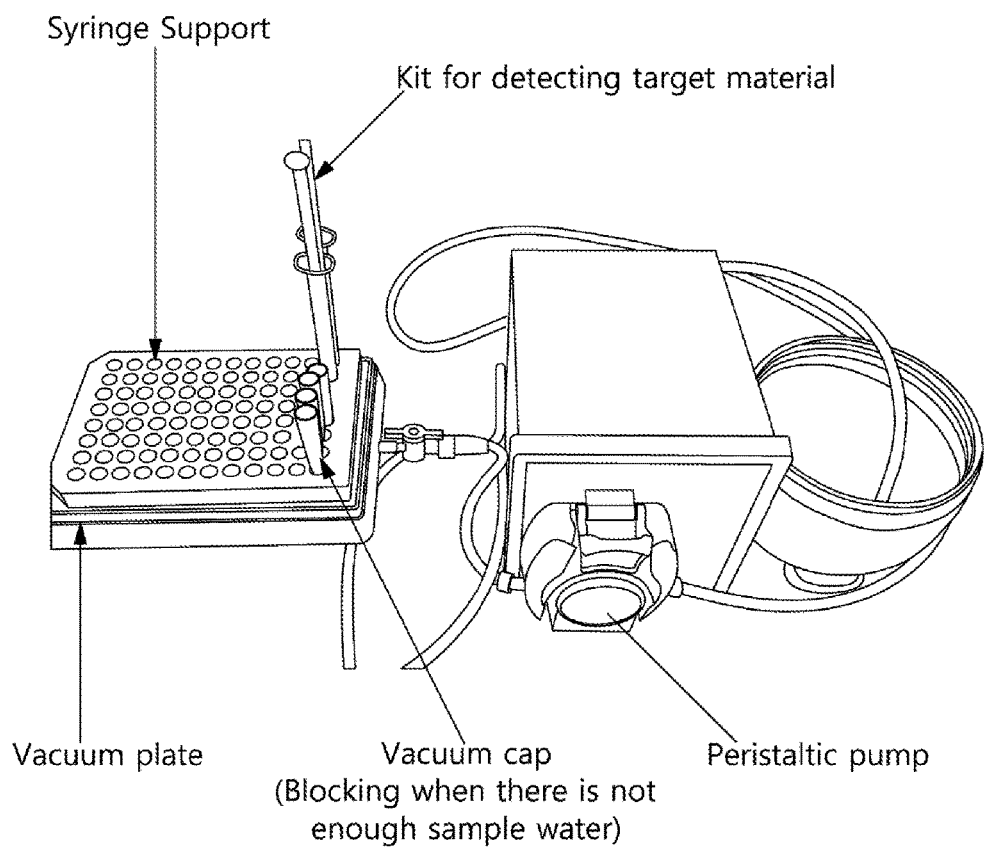
FIG. 5 is a photograph showing a vacuum device for removing the remaining reaction solution from the sample reaction unit.
Figure 6:
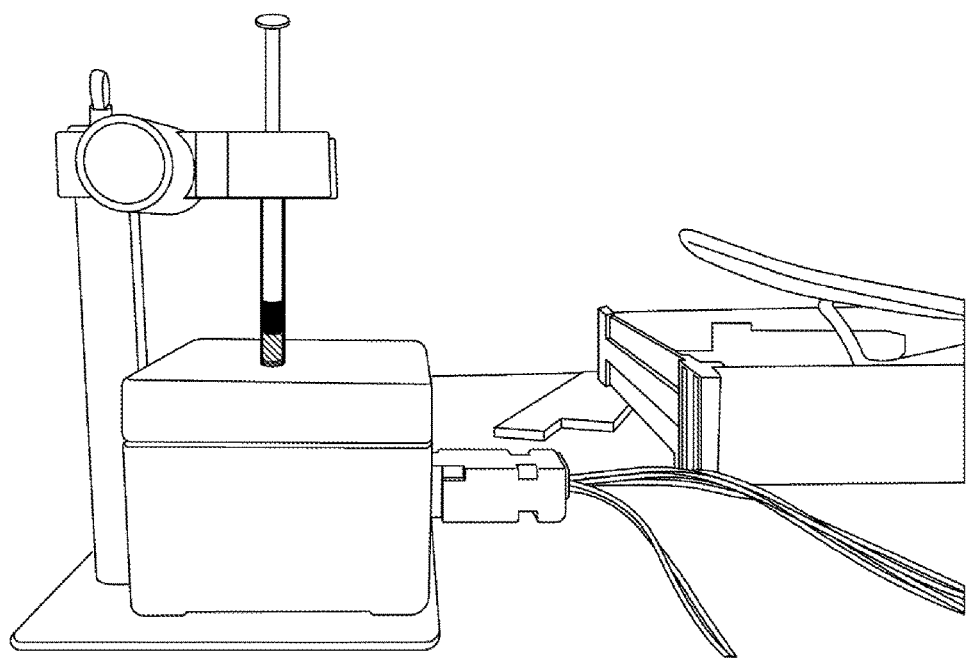
FIG. 6 is a photograph for the measurement of a magnetic signal of the kit for detecting a target material according to the present invention.

Hereinafter, a detailed description will be given of the present invention.

The present invention addresses a kit for detecting a target material, comprising a hollow tube-shaped body, a sample injection port, a sample injection member, a first support, a first sample reaction unit, and a second support.

Here, the front end of the body is provided with the sample injection port.

The portion of the front end of the body, other than the sample injection port, is closed.

The rear end of the body is formed with an opening into which the sample injection member is inserted.

The body includes the first support, the first sample reaction unit and the second support, which are inserted therein.

The first sample reaction unit is disposed between the first support and the second support.

The first support is disposed so that the first sample reaction unit is not exposed to the front end of the body and the sample injection port.

The second support is disposed so that the first sample reaction unit is not exposed to the opening of the body.

The first sample reaction unit is a polymer thin film including magnetic nanoparticles on which an antibody specifically binding to the target material is immobilized.

The polymer thin film is wound in a roll shape so as to form a hollow hole in a center thereof.

The central axis of the hollow hole is positioned perpendicular to the direction of injection of a sample.

The body 1 is provided in the form of a hollow tube, and has a shape that facilitates the application of pressure and the injection of a sample or some buffer solution. In the present invention, the type of body is not particularly limited so long as it is in the form of a hollow tube. Preferably used is a syringe.

The sample injection port 2 is formed at the front end of the body, whereby the sample is injected therethrough so as to be transferred to the first support 4. Furthermore, the portion of the front end of the body, other than the sample injection port, is closed.

The sample injection member 3 is inserted into the opening 7 formed in the rear end of the body, and the sample injection member is moved in the same direction as the direction of injection of the sample, whereby the sample may be injected into the kit for detecting a target material.

The first support 4, the first sample reaction unit 5 and the second support 6 are inserted and disposed inside the body, and the first sample reaction unit is disposed between the first support and the second support so that the first sample reaction unit is prevented from escaping from the kit.

Also, the first support is positioned so that the first sample reaction unit is not exposed to the front end of the body and the sample injection port, and the second support is positioned so that the first sample reaction unit is not exposed to the opening of the body.

The kinds of first support and second support are not limited so long as they are porous materials, and preferably useful is at least one selected from the group consisting of sterile sponge and glass fiber.

The first sample reaction unit may be a polymer thin film including magnetic nanoparticles on which an antibody specifically binding to a target material is immobilized, and the polymer thin film is wound in a roll shape so as to form a hollow hole in the center thereof, and the central axis of the hollow hole is positioned perpendicular to the direction of injection of the sample.

In the present invention, depending on the extent to which the polymer thin film is wound in a roll shape, the area of the first sample reaction unit may be easily changed, and a winding process is preferably conducted so that the hollow hole is not formed or is formed to be very small. If the size of the hollow hole is large, the flow rate at which the sample is injected through the sample injection port is excessively increased, and the loading area of the magnetic nanoparticles having the antibody immobilized thereon may decrease, making it difficult to detect the target material.

Also, the magnetic nanoparticles on which the antibody specifically binding to the target material is immobilized are loaded on the polymer thin film, after which the polymer thin film is wound in a roll shape, thereby not only easily changing but also maximally ensuring the area on which the magnetic nanoparticles having the antibody immobilized thereon are loaded, and thus the target material may be detected in a very large amount.

In the present invention, the extent of winding of the polymer thin film is not particularly limited, and may be easily adjusted depending on the kind or concentration of the target material.

The polymer thin film includes at least one selected from the group consisting of a nitrocellulose membrane, nylon, and polyvinylidene difluoride polystyrene.

In the kit for detecting a target material according to the present invention, the first sample reaction unit includes magnetic nanoparticles on which the antibody specifically binding to the target material is immobilized, whereby the sample may react with the antibody immobilized on the magnetic nanoparticles, thus detecting the sample through changes in the magnetism of the magnetic nanoparticles.

The antibody may be immobilized on the magnetic nanoparticles using a typical process, and preferably, the surface of magnetic nanoparticles is coated with a protein, and the antibody may be immobilized on the surface of the protein.

The protein functions to easily immobilize the antibody on the surface thereof without any modification process, and may include, without being limited to, at least one selected from the group consisting of streptavidin, peroxidase, glucose oxidase, choline oxidase, alkaline phosphatase, skim milk, serum, and peptide.

The kind of magnetic nanoparticles is not particularly limited, but the magnetic nanoparticles preferably include super-paramagnetic nanoparticles and may have a particle diameter of 10 to 100 nm.

Also, the target material includes at least one selected from the group consisting of an antigen, nucleic acid, virus and cell.

Also, the kit for detecting the target material according to the present invention may further include a second sample reaction unit and a third support inside the body.

The second sample reaction unit is positioned so as not to be exposed to the first sample reaction unit, and the third support is positioned so as not to expose the second sample reaction unit to the opening in the body.

When the second sample reaction unit is further included, different kinds of magnetic nanoparticles specifically binding to the target material may be contained in the first sample reaction unit and the second sample reaction unit, respectively, making it possible to simultaneously detect various kinds of target materials. For example, various kinds of target materials such as AI virus may be detected.

Thus, the kit for detecting the target material according to the present invention is able to detect one or more target materials.

The kit for detecting the target material according to the present invention is configured such that the sample reaction unit is inserted into the body of the kit and is not affected by external environmental factors, and is thus effectively useful in the measurement of infectious disease, etc.

Also, no additional testing device is required, and the kit of the invention may be easily used outdoors.

In addition, the present invention addresses a method of detecting a target material, comprising detecting whether or not the target material is present by injecting a sample into the kit of the present invention.

When the sample injection member of the kit of the present invention is moved in the direction of injection of the sample, the sample is injected into the body of the kit through the sample injection port, and the injected sample may react with the magnetic nanoparticles having the antibody immobilized thereon in the sample reaction unit through the first support comprising a porous material, whereby the presence of the target material may be detected through a signal of the magnetic nanoparticles.

Upon the reaction between the sample and the magnetic nanoparticles having the antibody immobilized thereon, a signal is analyzed using an electromagnetic device, thereby detecting the presence of the target material.

The detection method enables the sample to be analyzed while being injected.

A better understanding of the present invention may be obtained via the following examples that are merely set forth to illustrate, but are not to be construed as limiting the scope of the present invention.

Preparation Example 1. Detection of Target Material

A nitrocellulose membrane having a size of 8×12 cm was placed in 10 mL of a streptavidin solution having a concentration of 50 µg/mL for 5 min, thus manufacturing a first sample reaction unit.

A nitrocellulose membrane having a size of 8×12 cm was placed in 10 mL of a biotin solution having a concentration of 50 µg/mL for 5 min, thus manufacturing a second sample reaction unit.

The remaining reaction solutions were removed from the first sample reaction unit and the second sample reaction unit using a vacuum device.

Thereafter, the first sample reaction unit and the second sample reaction unit were placed in 10 mL of a 3% BSA (bovine serum albumin) solution and a PBS (phosphate-buffered saline) solution containing 1% sodium azide ($NaN_3$).

Thereafter, the first sample reaction unit and the second sample reaction unit were wound in a roll shape.

The first support, the first sample reaction unit, the second support, the second sample reaction unit and the third support were sequentially inserted upward into a syringe, thus manufacturing a kit for detecting a target material. Here, the first, second, and third supports were sterile sponge.

A solution of magnetic nanoparticles having a particle diameter of 50 nm and surface-modified with biotin (fluidMAG-Biotin, available from Chemicell) was prepared.

400 µL of the solution was injected into the kit and allowed to stand for 5 min, and the process of injecting 1 mL of the PBS solution into the kit was repeated five times.

Thereafter, the kit was measured using an FMMD meter to analyze the signal of the magnetic nanoparticles (H.-J. Krause et al./Journal of Magnetism and Magnetic Materials 311 (2007) 436-444).

Furthermore, the signal of magnetic nanoparticles was analyzed in the same manner as above, with the exception that surface-non-modified magnetic nanoparticles were used. The results of the first sample reaction unit and the second sample reaction unit are shown in Table 1 below.

TABLE 1

| Classification | First sample reaction unit | | Second sample reaction unit | |
|---|---|---|---|---|
| | Average 5 times Analysis | SDV | Average 5 times Analysis | SDV |
| Kit before measurement | 0 | ±2.5 | 0 | ±2.5 |
| Magnetic nanoparticles | 9.6 | ±2.6 | 8.9 | ±3.6 |
| Magnetic nanoparticles surface-modified with biotin | 100 | ±4.5 | 7.3 | ±3.5 |

Streptavidin is bound to biotin.

The above results are obtained by normalizing the measured values to the reference value at which the signal of the magnetic nanoparticles was set as 100.

As is apparent from the results of Table 1, the magnetic nanoparticles surface-modified with biotin reacted with streptavidin loaded on the first sample reaction unit, and no reaction occurred in the biotin-loaded second sample reaction unit.

Also, the surface-non-modified magnetic nanoparticles did not react in the first sample reaction unit and the second sample reaction unit.

Therefore, the kit for detecting the target material according to the present invention is configured such that different materials are loaded on respective sample reaction units, thus enabling the detection of various target materials.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A kit for detecting a target material, comprising:
   a hollow tube-shaped body;
   a sample injection port;
   a sample injection member;
   a first support;
   a first sample reaction unit; and
   a second support,
   wherein a front end of the body is provided with the sample injection port,
   a portion of the front end of the body, other than the sample injection port, is closed,
   a rear end of the body is formed with an opening into which the sample injection member is inserted,
   the body includes the first support, the first sample reaction unit and the second support, which are inserted therein,
   the first sample reaction unit is disposed between the first support and the second support,
   the first support is disposed so that the first sample reaction unit is not exposed to the front end of the body and the sample injection port,
   the second support is disposed so that the first sample reaction unit is not exposed to the opening of the body,
   the first sample reaction unit is a polymer thin film including magnetic nanoparticles on which an antibody specifically binding to the target material is immobilized,
   the polymer thin film is wound in a roll shape so as to form a hollow hole in a center thereof, and
   a central axis of the hollow hole is positioned perpendicular to a direction of injection of a sample.

2. The kit of claim 1, wherein the target material includes at least one selected from the group consisting of an antigen, nucleic acid, a virus, and a cell.

3. The kit of claim 1, wherein the magnetic nanoparticles include super-paramagnetic nanoparticles.

4. The kit of claim 1, wherein the magnetic nanoparticles have a particle diameter of 10 to 100 nm.

5. The kit of claim 1, wherein the support includes at least one selected from the group consisting of sponge and glass fiber.

6. The kit of claim 1, wherein the polymer thin film includes at least one selected from the group consisting of a nitrocellulose membrane, nylon, and polyvinylidene difluoride polystyrene.

7. The kit of claim 1, wherein a surface of the magnetic nanoparticles is coated with a protein, and the antibody is immobilized on a surface of the protein.

8. The kit of claim 7, wherein the protein includes at least one selected from the group consisting of streptavidin, peroxidase, glucose oxidase, choline oxidase, alkaline phosphatase, skim milk, serum, and peptide.

9. The kit of claim 1, further comprising a second sample reaction unit and a third support,
wherein the second sample reaction unit and the third support are inserted into the body,
the second sample reaction unit is disposed so as not to be exposed to the first sample reaction unit, and
the third support is disposed so that the second sample reaction unit is not exposed to the opening of the body.

10. A method of detecting a target material, comprising detecting whether or not the target material is present by injecting a sample into the kit of claim 1.

11. The method of claim 10, wherein the sample is injected through a sample injection port of the kit and detected in a sample reaction unit of the kit.

* * * * *